United States Patent [19]

Luther

[11] Patent Number: 4,668,221
[45] Date of Patent: May 26, 1987

[54] ASSEMBLY OF STYLET AND CATHETER

[75] Inventor: Ronald B. Luther, Newport Beach, Calif.

[73] Assignee: Luther Medical Products, Inc., Santa Ana, Calif.

[21] Appl. No.: 749,281

[22] Filed: Jun. 27, 1985

Related U.S. Application Data

[63] Continuation-in-part of Ser. No. 717,159, Mar. 28, 1985, Pat. No. 4,610,671.

[51] Int. Cl.⁴ .............................................. A61M 5/18
[52] U.S. Cl. ................................... 604/164; 604/166; 604/168; 604/265
[58] Field of Search .................. 604/43, 44, 160, 164, 604/166, 168, 170, 900, 264–266, 280, 281; 128/341, 343, 768; 264/41

[56] References Cited

U.S. PATENT DOCUMENTS

| | | | |
|---|---|---|---|
| 3,063,451 | 11/1962 | Kowalk | 604/411 |
| 3,566,874 | 3/1971 | Shepherd et al. | 604/265 |
| 3,598,127 | 8/1971 | Wepsie | 604/265 |
| 3,995,623 | 12/1976 | Blake et al. | 128/768 |
| 4,072,146 | 2/1978 | Howes | 128/768 |
| 4,183,884 | 1/1980 | Wichterle et al. | 264/41 |
| 4,381,380 | 4/1983 | LeVeen et al. | 604/265 |
| 4,392,848 | 7/1983 | Lucas et al. | 604/265 |
| 4,406,656 | 9/1983 | Hattler et al. | 604/43 |
| 4,479,795 | 10/1984 | Mustacich et al. | 604/265 |

Primary Examiner—C. Fred Rosenbaum
Assistant Examiner—Jerome R. Smith, Jr.
Attorney, Agent, or Firm—Willie Krawitz

[57] ABSTRACT

A grooved stylet having a puncture point aligned with the stylet axis is mounted through a catheter to form an assembly. The aligned puncture point enables more accurate piercing of a vein, and reduces the possibility of double piercing the vein.

The stylet near its proximal end is provided with a circular shoulder which abuts the proximal end of the catheter, and the catheter end is positioned on the stylet so that only the stylet puncture point projects beyond the catheter.

The catheter is constructed of a hydrophilic polymer which expands away from the stylet and permits the stylet to be withdrawn from the puncture site, leaving the catheter in place in the vein.

If desired, a plurality of bores may be provided in the catheter for separate attachment to different I.V. solutions; this enables various solutions to be fed at different rates to the patient through a single I.V. puncture site.

5 Claims, 19 Drawing Figures

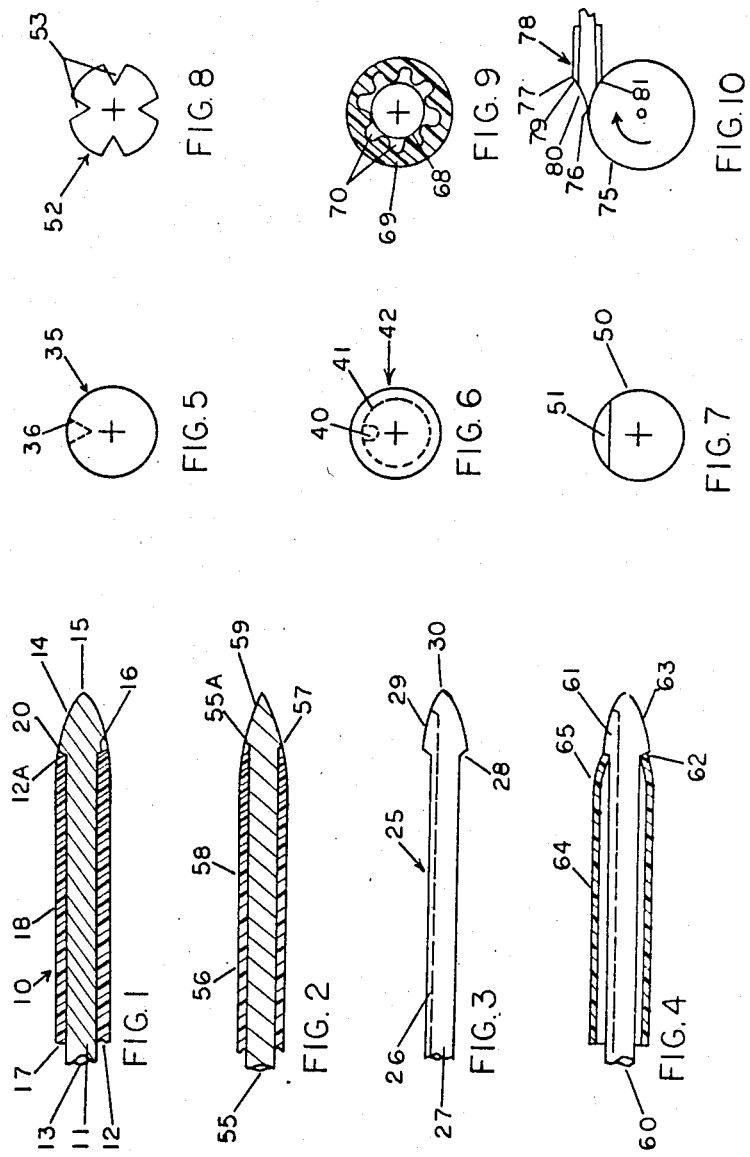

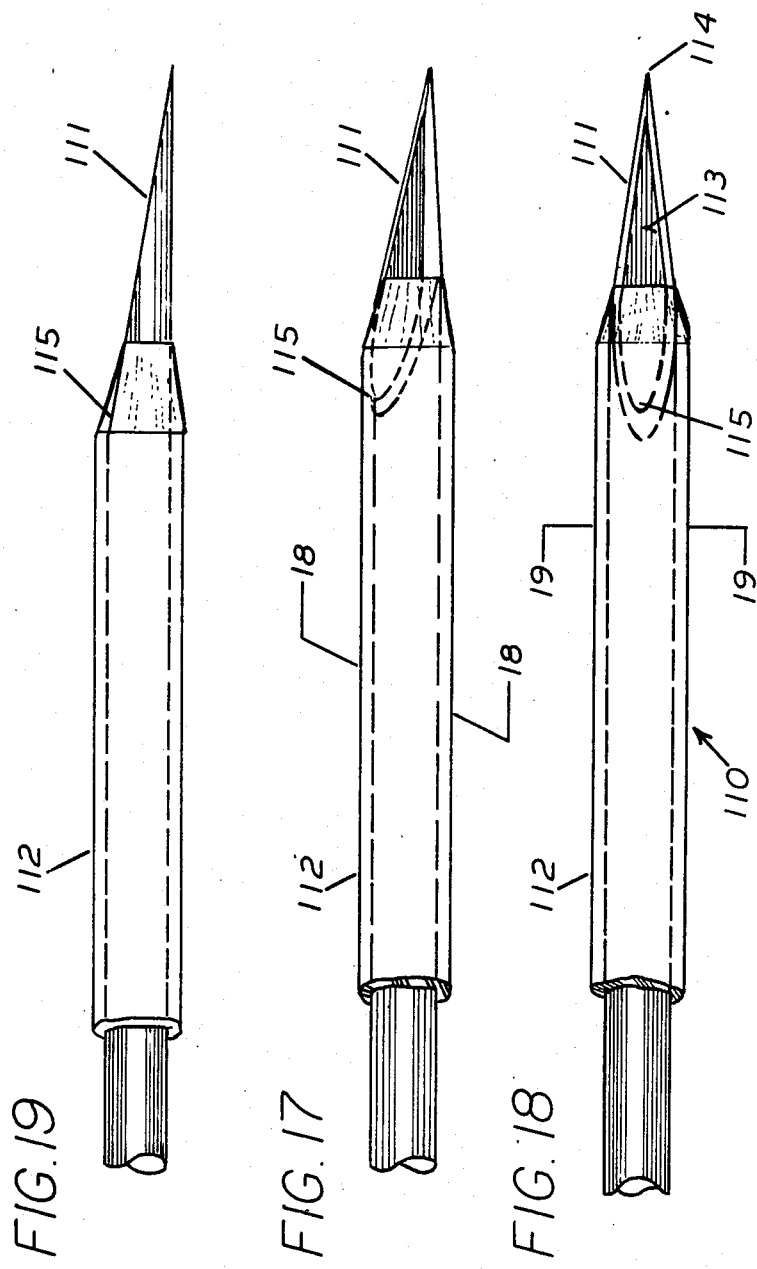

ASSEMBLY OF STYLET AND CATHETER

BACKGROUND OF THE INVENTION

This invention is a continuation-in-part of U.S. Ser. No. 717,159 filed Mar. 28, 1985, now U.S. Pat. No. 4,610,671, entitled: "Assembly of Stylet and Catheter", inventor: Ronald B. Luther.

This invention relates to a new and improved assembly for insertion of a catheter into a patient. More specifically, this invention relates to a stylet providing an axially aligned puncture tip, the stylet being inserted through a catheter to form an assembly which can effectively pierce a vein. Upon withdrawal of the stylet, the catheter remains in place in the vein.

Presently manufactured hypodermic needles, cannula, and other needles employ a ground needle tip having an off-axis alignment from the longitudinal needle axis. This enables a relatively even needle tip bevel to be formed. These off-axis tips present a problem in that insertion of the needle into the vein of a patient or user must be in an off-axis alignment mode, and this can lead to the needle double penetrating the wall of a vein. This is due to the inherent longer length of the needle tip beyond the catheter.

Another problem of employing a hollow needle with a catheter inserted therein is that upon insertion into a vein, there exists the possibility of the catheter double puncturing the vein.

Another problem associated in using a cannula or hypodermic needle is the necessity to manufacture the central bore of the needle, and in an accurate manner.

Another problem with prior art needles and cannula is that flashback of blood into the needle is not observed until the blood reaches the distal end or hub portion of the needle.

It would be preferable to provide an assembly including a catheter and vein piercing device such that flashback is observed almost immediately, i.e., near the puncture tip rather than at the distal end, or hub of the assembly.

It would be preferred to form a puncture tip that not only has an even bevel, but in which the tip is axially aligned with the central longitudinal axis of the vein piercing device and the catheter. This longitudinal alignment reduces the possibility of double puncturing the vein.

Another problem with prior art needles is due to coring, and can result in blockage of a needle, or subsequent embolism in a vein, artery, etc. It would be preferred to manufacture a vein piercing device that does not require formation of a hollow bore, and thereby would eliminate the possibility of coring.

Furthermore, it would be desireable to manufacture a vein piercing assembly that minimizes or reduces the possibility of double puncturing a vein or artery by minimizing the amount of exposed puncturing tip in front of the catheter.

Present over-the-needle catheters have at least two problems: i. they have a proximal end shoulder, which makes it difficult to insert the catheter into a vein; and, ii. the catheters remain stiff when in place in the vein, and this causes patient trauma. It would be desireable to manufacture a vein piercing assembly in which the vein piercing element is adapted to easily pierce the vein and then be removed, leaving behind a soft associated catheter in the vein, with reduced trauma.

It would be also desireable to provide multiple I.V. feeds to a patient through a single vein penetration. Usually, different solutions of medications require different feed rates over different time intervals. Hence, supplying various medications from a single solution is not possible, given these constraints.

THE INVENTION

According to the invention, there is provided a vein piercing assembly of a catheter and inserted stylet. Since the stylet is solid, it can be formed at one end into a puncture tip having a uniform bevel, while at the same time being aligned with the central longitudinal axis of the stylet. This enables the stylet to be inserted into the vein, with the tip being aligned to the central axis of the stylet, rather than being off-aligned to the central axis. Furthermore, the stylet may be provided with an external longitudinal notch or notches, groove, flatspot, etc., which form a space between the stylet and external catheter. Flashback occurs along this longitudinal notch and can be seen almost immediately when it occurs, and this enables the user to quickly determine when the vein has been pierced.

The catheter is manufactured from a hydrophilic polymer that expands when it contacts blood in the vein. During expansion of the catheter, the stylet can be retracted leaving the catheter in place. The catheter then further expands along its axis when fluid from the attached intravenous administration solution is fed from a fluid container and a plastic I.V. set through the expandable catheter to the patient's system. Upon expansion, the hydrophilic polymer becomes soft, with a durometer hardness less than about 70 SHORE A; this tends to reduce trauma in the vein.

The assembly of this invention enables a reduction of about 30%–60% in puncture tip length, compared to conventional needle tips. Thus, for a stylet length of about 1"–6", puncture tip lengths will correspondingly vary from about 0.04"–0.12".

When employed as an assembly of a needle and an over-the-needle catheter, problems associated with catheter slippage on insertion of the needle into a vein, can be reduced. Also, the possibility of 'coring' caused by the bevel portion of the needle, can be reduced by shrink fitting of the catheter over the distal portion of the needle bevel.

When the catheter is constructed with a plurality of bores, it may be used to feed different I.V. solutions to the patient over differing time intervals through a single vein penetration; this arrangement presents far less trauma for the patient, and less opportunity for infection. The feeding of multiple solutions from separate sources also avoids potential problems arising from combining solutions due to the formation of precipitates, colloids, crystalloids, etc.

BRIEF DESCRIPTION OF THE DRAWINGS

FIG. 1 is a sectional side elevation in axial section of the assembly of a stylet and catheter according to the invention;

FIG. 2 is a sectional side elevation in axial section of another embodiment of the catheter and stylet assembly of this invention;

FIG. 3 is a sectional side elevation in axial section of an embodiment of the invention showing a grooved stylet;

FIG. 4 is a sectional side elevation in axial section of the stylet showing different embodiments of the stylet and catheter;

FIGS. 5–8 are sectional views in end elevation showing various forms of recesses or grooves along the stylet axis;

FIG. 9 is a sectional view in end elevation showing another embodiment of a catheter for the stylet;

FIG. 10 is a sectional view in side elevation showing the simultaneous maching of a stylet and catheter to produce an assembly having a uniformly curved surface between the catheter and the stylet;

FIG. 17 is a side elevation view, partly in external perspective, showing an assembly of a needle and over-the-needle catheter;

FIG. 18 is a top view of FIG. 17, taken along the lines 18—18 of FIG. 17; and,

FIG. 19 is an external view in side elevation, taken along the lines 19—19 of FIG. 18.

DESCRIPTION OF THE PREFERRED EMBODIMENTS

Figure 12:
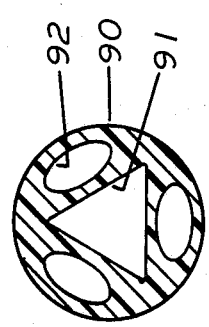
FIGS. 11–16 are transverse sectional views of various catheter configurations following expansion of the catheter due to hydration with blood, to provide a plurality of separate feed bores to a patient.

The catheter and stylet assembly 10 of this invention is shown in FIGS. 1, 2, 4, 6 and 9, and includes a configured stylet 11 over which is positioned a contoured catheter 12. The stylet is solid and may be manufactured of a stainless steel such as 304–316; typically, a stainless steel such as 304 may be used. Harder materials such as tungsten are also suitable, and possibly carbon fiber, alone or reinforced with resin. The stylet 11 includes a distal end 13, a rounded proximal end 14 having a vein or artery piercing tip 15, and a forwardly inclined circumferential shoulder 16.

The catheter 12 at its proximal end 12a, abuts the shoulder 16 and is restrained thereby from further movement towards the piercing tip 15. In addition, the catheter wall thickness is sized, and the catheter itself is shaped to define an overall continuous and uniformly curved outer surface 16 extending from the distal end 17 of the catheter to the rounded proximal end 14 and tip 15. Also, the interface 20 at the stylet shoulder 16 and the outer surface 18 of the catheter is essentially smooth.

The catheter is constructed of a hydrophilic polymer which expands upon contact with water. Publications disclosing hydrophilic polymers include: U.S. Pat. Nos. 3,822,238; 3,975,350; 4,156,066; 4,156,067; 4,255,550; 4,408,023; 4,424,305; 4,439,583; 4,439,584; 4,439,554; and, 4,439,558.

Typical bore sizes of the catheter vary about 36 gauge and larger; wall thicknesses are designed to minimize kinking and may be derived from known formulae.

As shown in FIGS. 3, 4, and 5–7, the stylet may be provided with a groove to produce flashback when the stylet is inserted into a vein, artery, organ, or the like. FIGS. 1 and 2 show embodiments of the assembly which do not use a flashback groove.

As shown in FIG. 3, a stylet 25 provides a groove 26 which extends from the distal end 27 through a catheter retaining shoulder 28, at the proximal end 29, and which terminates near the tip 30.

FIGS. 5–8 illustrate various types of groove configurations that may be used for the stylet. In FIG. 5, a stylet 35 is shown with a V-notch shaped groove 36. A U-shaped groove 40 and octagonally shaped tip 40a are employed for the stylet 41 in FIG. 6, and a catheter 42 is positioned around the periphery of the stylet. If desired, the tip and catheter are ground together during manufacturing. Consequently, when blood flashes back along the groove after insertion of the stylet into a vein or artery, it will be contained within the groove by the catheter. Also, since the catheter is transparent or partially transparent, this flashback will be observable immediately, and will enable the user to determine that the patient's (or user's) vein has been penetrated.

In FIG. 7, the stylet 50 provides a flat portion 51 which functions in the same manner as V or U-shaped grooves. As in FIG. 6, when the stylet is surrounded by a catheter, flashback blood will both be contained by the catheter and will be observable immediately upon penetration into the vein.

FIG. 8 shows a stylet 52 having a plurality of grooves 53 disposed at about 90° around the periphery of the stylet. For an outside stylet diameter of about 0.017", and with four grooves at 90° to each other, each triangular groove is sized about 0.004" at the base, and 0.003" deep.

FIGS. 2, 4 and 9 illustrate different types of catheters which may be utilized with a stylet. In FIG. 2, a stylet 55 is shown that is insertably mounted within a catheter 56. The longitudinal flashback groove is absent from this embodiment. A forward shoulder 55a near the proximal end of the stylet is much shallower than the corresponding shoulders in FIGS. 1 and 3. Hence, the proximal end 57 of the catheter will have a very small wall thickness in order to maintain a uniform curvature along the outer sidewall 58 of the catheter and the proximal end exterior surface 59.

In FIG. 4, the stylet 60 employs a flashback groove 61, and the circular retaining shoulder 62 at the proximal end 63 is inclined backwardly. This results in the catheter 64 becoming outwardly stressed, or buckled, at its proximal end 65.

FIG. 9 illustrates a stylet 68 similar to that of FIGS. 1 and 2 i.e., having no groove. A catheter 69 surrounds the stylet, and provides a plurality of inner grooves 70 along which blood flashback occurs. This construction is less expensive than machining a metal stylet since the grooves 70 can be formed by a plastic extrusion process rather than an expensive metal grooving process.

FIG. 10 shows a manufacturing process using a grinding wheel, a portion 75 of which is shown, to form a stylet puncture tip 76 and simultaneously configure the proximal end 77 of a catheter 78. The grinding wheel produces a uniformly curved puncture tip surface 79, 80 along the leading edge of the catheter and the stylet tip, respectively. No discontinuity occurs at the junction 81 between the inner wall of the catheter and the stylet. Consequently, insertion of the catheter into a vein is not impeded by the presence of a proximal catheter shoulder.

In operation, the stylet and catheter are inserted into a vein, artery, organ, or the like. If the catheter is to remain in place in the vein when the stylet is withdrawn, the proximal end of the catheter must be dislodged from the position against the proximal shoulder of the stylet when the stylet tip is still located in the vein. As previously indicated, a hydrophilic polymer is used as the material of construction of the catheter. Consequently, when the stylet is inserted into the vein, contact of the catheter with blood will cause the catheter tip to expand out of contact from the shoulder of the stylet. When the stylet is retracted, the catheter will remain in place in the user's vein.

FIGS. 11–16 illustrate various catheter configurations following hydration due to contact with blood, and expansion of the catheter into its final configuration.

Figure 11:

In FIG. 11, the catheter 85 is shown having a central area 86 that derives its shape from that of the extrusion mandrel over which it is formed, by conventional extrusion techniques. A plurality of circular bores 87 are provided through which flow various I.V. solutions. Prior to expansion due to hydration, resulting from contact with blood, the dehydrated catheter has a much more constricted appearance compared to FIG. 11, and the bores appear somewhat as slits.

Figure 14:
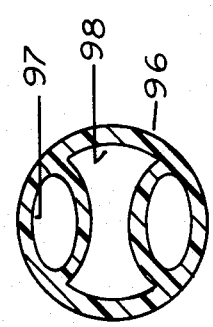
Figure 13:
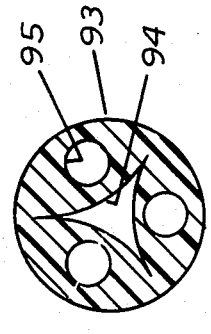
Figure 15:
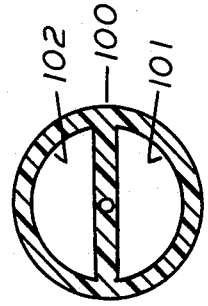
Figure 16:
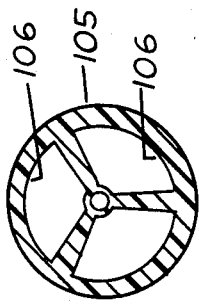

In FIG. 12, the catheter 90 provides a central area 91 and elliptical bores 92. In FIG. 13, the catheter 93 provides a central area 94 and circular bores 95. In FIG. 14, the catheter 96 defines two elliptical bores 97, and a central area 98. In FIG. 15, the catheter 100 is shown after hydration with blood to define two half-circle bores 101, 102. In FIG. 16, the catheter 105 defines curved triangular bores 106, following hydration with blood.

Following expansion due to hydration, the open end of the catheter is slit to expose the bores which are then connected to I.V. tubes. The center section can be plugged, or used as an additional I.V. feed bore.

In FIGS. 17–18, there is shown an assembly 110 of an over-the-needle catheter embodiment of this invention. The assembly includes a needle 111, and an expandable catheter 112. The needle includes a bevel portion 113 terminating in a tip 114 and a curved distal bevel portion 115. The catheter 112 is shrunk by dehydration to occlude the bevel portion 115 and prevent coring when inserted into the vein. Also, as shown in FIG. 19, the shrink fit over the bevel portion 115 increases gripping effects between the catheter and needle, and minimizes slipping when the needle is inserted. Upon contact with blood, the catheter expands due to hydration, and the needle is removed leaving the catheter in place.

If desired, the polymer formulation can be varied to produce different expansion sizes to accommodate for different patient size requirements, using a single initial bore size. By contrast, present over-the-needle catheters remain constant in diameter, and hence, different uses require different initial bore sizes.

In addition, a time release medication may be incorporated into the polymer. The medication is subsequently leached out by passage of the I.V. fluid, and provides small amounts of a high concentration of a disinfectant and/or bacteriostat, fungicide, antiobiotic, etc., at the puncture site. This leaching out cannot be duplicated with present day catheters which are manufactured of non-leachable materials such as polyvinyl chloride, TEFLON, polyurethane, polyethylene, etc.

Thus, the assembly of this invention provides a catheter which becomes relatively soft and flexible compared to prior art over-the-needle catheters, and reduces trauma when in the vein. Also, the present invention minimizes problems of entering the end of the catheter into the vein.

I claim:

1. An assembly for piercing a vein, artery, organ, and the like, comprising:
   a. a needle defining an outer surface, distal and proximal ends, and a bevel portion including a curved distal area;
   b. a puncture tip formed at the proximal end of the needle;
   c. a catheter comprising a hydrophilic polymer disposed over the needle, the catheter defining an inner surface, a distal end, and a proximal end in contact with, and occluding the curved distal area, the inner surface being in close contact with the outer surface of the needle, whereby, the catheter and needle are enabled to enter a puncture site with reduced 'coring' and slippage, and upon contact with liquid in the puncture site, the catheter will expand and enable the needle to be withdrawn, leaving the catheter in place in the puncture site.

2. The assembly of claim 1, in which the catheter is shrink fitted over the distal area and outer surface of the needle.

3. The assembly of claim 1, in which the catheter provides a sidewall and a plurality of I.V. bores defined therein.

4. The assembly of claim 1, in which a time release medication is incorporated into the catheter, and the medication is adapted to be leached out by passage of I.V. fluid.

5. The assembly of claim 1, in which the catheter provides a hardness of less than about 70 SHORE A.

* * * * *